(12) United States Patent
Conroy (10) Patent No.: US 8,535,286 B2
(45) Date of Patent: Sep. 17, 2013

(54) VIBRATING TAMPON APPARATUS WITH REMOTE CONTROL

(75) Inventor: David Conroy, Brooklyn, NY (US)

(73) Assignee: Marlafin AG, Hagendorn (CH)

( * ) Notice: Subject to any disclaimer, the term of this patent is extended or adjusted under 35 U.S.C. 154(b) by 753 days.

(21) Appl. No.: 11/743,263

(22) Filed: May 2, 2007

(65) Prior Publication Data

US 2007/0260210 A1    Nov. 8, 2007

Related U.S. Application Data

(60) Provisional application No. 60/746,194, filed on May 2, 2006.

(51) Int. Cl.
*A61F 13/20* (2006.01)

(52) U.S. Cl.
USPC ............ 604/385.18; 604/904; 601/43

(58) Field of Classification Search
USPC ............ 604/385.18, 904; 601/46–83
See application file for complete search history.

(56) References Cited

U.S. PATENT DOCUMENTS

| | | | | |
|---|---|---|---|---|
| 3,669,100 A | * | 6/1972 | Csanad | 601/46 |
| 5,573,499 A | * | 11/1996 | McAllister | 601/70 |
| 5,782,779 A | | 7/1998 | Kilgore | |
| 6,183,428 B1 | | 2/2001 | Kilgore | |
| 6,899,700 B2 | * | 5/2005 | Gehling et al. | 604/285 |
| 2003/0171702 A1 | * | 9/2003 | Thompson et al. | 601/72 |
| 2004/0082886 A1 | * | 4/2004 | Timpson | 601/15 |

* cited by examiner

*Primary Examiner* — Lynne Anderson
(74) *Attorney, Agent, or Firm* — Hovey Williams LLP

(57) ABSTRACT

A vibrating tampon apparatus to provide relief from feminine menstrual cramps comprises a vibration element, a housing unit, and a tampon member. The vibration element provides a source of vibrations and is contained within the housing unit. The tampon member is fabricated of an absorbent material and covers at least a portion of the housing unit, while being held in place by retaining elements on the exterior of the housing unit. Electric power is supplied to the vibration element by a remote electric power source. The electrical connection between the electric power source and the vibration element is controlled remotely by a control unit that allows the apparatus to operate either momentarily, in a testing situation, or continually for the lifetime of the electric power source, which is for normal usage and cannot be interrupted by the user.

24 Claims, 8 Drawing Sheets

VIBRATING TAMPON APPARATUS WITH REMOTE CONTROL

RELATED APPLICATIONS

The present application claims priority benefit to U.S. provisional patent application entitled "VIBRATING TAMPON APPARATUS WITH REMOTE CONTROL", Ser. No. 60/746,194, filed May 2, 2006. This provisional application is incorporated into the present application by reference.

BACKGROUND OF THE INVENTION

1. Field of the Invention

Embodiments of the present invention relate to sanitary napkin construction. More particularly, embodiments of the present invention relate to a sanitary napkin/tampon construction with a vibration mechanism incorporated therein and including a remote power source and controlling mechanism.

2. Description of the Related Art

One method of trying to relieve the pain from cramps that a woman suffers during menstruation is to directly stimulate the walls of the vaginal canal. Typically, this stimulation is achieved by constructing a sanitary napkin that includes a vibration mechanism. Prior art techniques have also included a power source for the vibration mechanism that is located external to the tampon apparatus. However, there is also a need for the ability to briefly turn the vibration mechanism on for testing purposes either during manufacture or before usage. Furthermore, there is a need to ensure that the absorbent tampon material is securely fastened to the vibration mechanism.

SUMMARY OF THE INVENTION

Embodiments of the present invention address the above-mentioned needs and provide a distinct advance in the art of sanitary napkin construction. More particularly, embodiments of the invention provide a one-time usage vibrating tampon apparatus that provides relief from feminine menstrual cramps and includes a remote controlling mechanism and absorbent material retaining elements.

In various embodiments, the present invention is a vibrating tampon apparatus to provide relief from feminine menstrual cramps and comprises a vibration element, a housing unit, and a tampon member. The vibration element provides a source of vibrations. The housing unit houses the vibration element and is assembled to be water resistant. The housing unit is covered at least in part by the tampon member and includes a plurality of external retaining elements that fasten the tampon member to the outside of the housing unit. The tampon member is fabricated of an absorbent material and the combination of the tampon member and the housing unit is appropriately dimensioned to be received in a female's vaginal canal.

Electric power is supplied to the vibration element from a remote electric power source, such as a battery. A control unit, collocated with the electric power source, controls an electrical connection between the electric power source and the vibration element.

In some embodiments, the control unit includes a removable cap, that when removed provides continuous operation of the apparatus for the lifetime of the electric power source. The control unit also includes a momentary button, that when activated provides temporary operation of the apparatus.

In other embodiments, the control unit includes a pushbutton, that when pushed with a lesser force provides temporary operation of the apparatus and when pushed with a greater force provides operation of the apparatus for the lifetime of the electric power source.

An electric cable provides an electrical connection between the control unit and the vibration element. Coupled to the electric cable is a mechanical cable that provides mechanical pull strength for a connection between the control unit and the housing unit to help ensure that the housing unit and tampon member can be safely removed from the female's vaginal canal after usage.

This summary is provided to introduce a selection of concepts in a simplified form that are further described below in the detailed description. This summary is not intended to identify key features or essential features of the claimed subject matter, nor is it intended to be used to limit the scope of the claimed subject matter.

Other aspects and advantages of the present invention will be apparent from the following detailed description of the preferred embodiments and the accompanying drawing figures.

BRIEF DESCRIPTION OF THE DRAWING FIGURES

Various embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figures 1, 2:
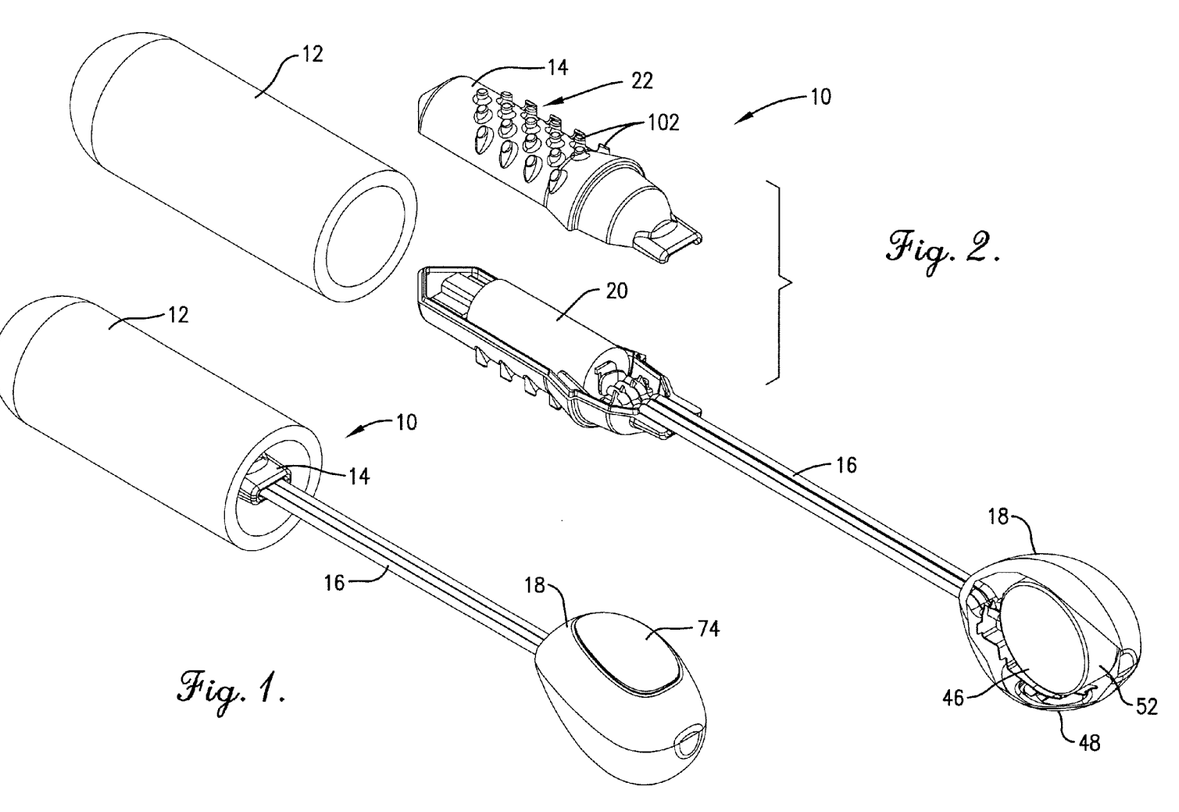
FIG. 1 is a perspective view showing an embodiment of the present invention.
FIG. 2 is an exploded perspective view showing an embodiment of the present invention.

FIG. 1 shows the vibrating tampon apparatus 10 which comprises a tampon member 12, a housing unit 14, a cable 16, and a control unit 18. FIG. 2 shows an exploded view of the apparatus 10, depicting the body of the housing unit 14 with a vibration element 20 included in the interior of the housing unit 14. FIG. 2 further shows the coupling of the cable 16 to the housing unit 14 and the control unit 18.

The tampon member 12 is generally of an elongated cylindrical shape, with a hemispherical dome on one end and is of such dimensions as to be comfortably received in a female's vaginal canal. The tampon member 12 is hollow and is open on the other end to allow access to the interior of the tampon member 12. Thus, when the housing unit 14 is inserted into the open end, the tampon member 12 will cover most of the housing unit 14 while still allowing the cable 16 to access the housing unit 14.

The tampon member 12 is generally fabricated from a soft absorbent compressed fibrous material such as cotton, rayon, or the like. The absorbent material of the tampon member 12 may also be coated or immersed with an analgesic or other medicaments to act as a topical agent to provide fast-acting relief upon contact with the walls of the vaginal canal.

Figures 3, 5:
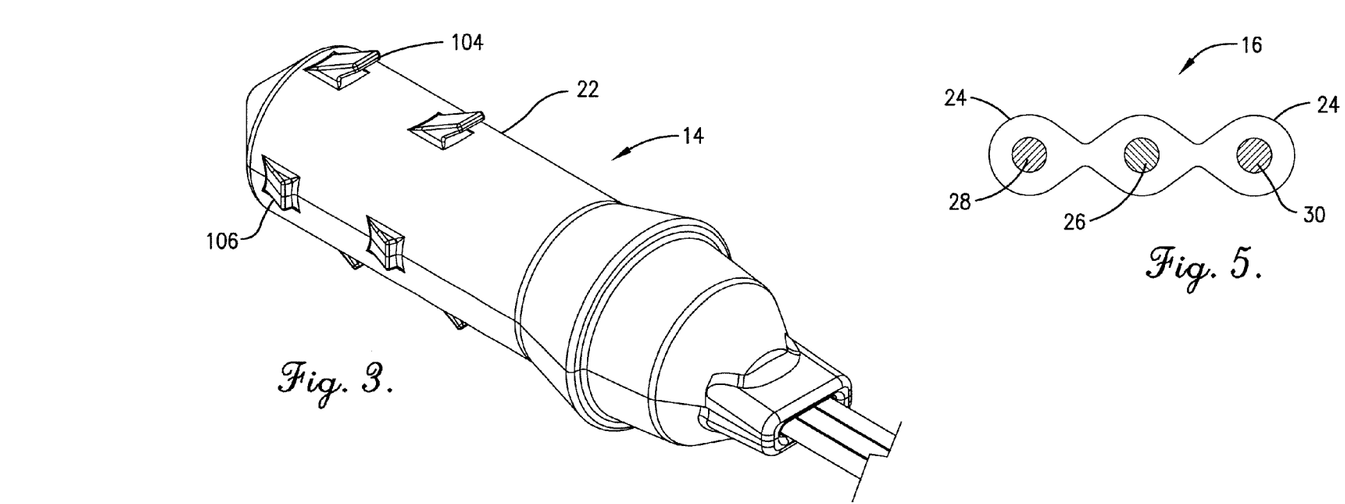
FIG. 3 is a perspective view of an embodiment of the housing unit.
FIG. 5 is a sectional view of a cable.

The housing unit 14 is generally cylindrical shaped to be able to receive the tampon member 12 as a covering and includes a plurality of retaining elements 22 along the sides of the cylinder. The retaining elements 22 may include, but are not limited to, barbs, nubs, stubs, and concentric rings. In general, the retaining elements 22 protrude from the exterior of the housing unit 14 in order to couple with the tampon member 12 and provide strong resistance to the removal of the tampon member 12 from the housing unit 14. One embodiment is shown in FIG. 2, wherein the retaining elements 22 are an array of stubbed protrusions 102. Each stubbed protrusion 102 is a small cylinder, accompanied by a raised portion at its base, attached to the surface of the housing unit 14. Another embodiment of the housing unit 14 is shown in FIG. 3, wherein the retaining elements 22 are a plurality of barbs 104 and nubs 106. Each barb 104 is an elongated tab that protrudes from the housing unit at an angle. Each nub 106 is a shortened tab that protrudes from the housing unit at an angle. For all embodiments, once the tampon member 12 covers the housing unit 14, the retaining elements 22 attach to the absorbent material and form a strong bond to retain the tampon member 12 on the housing unit 14. It is also possible that an adhesive may be applied to at least a portion of the exterior of the housing unit in order to aid in fastening the tampon member 12 to the housing unit 14.

Figure 4:
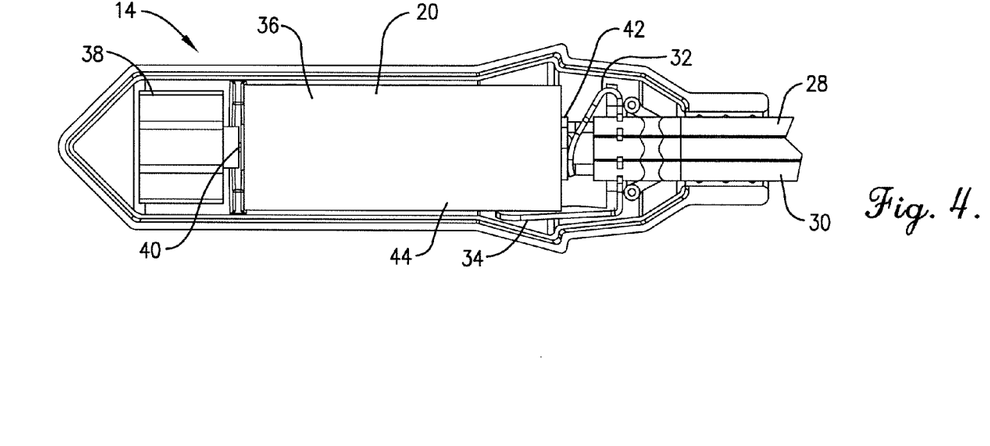
FIG. 4 is a top plan view of the interior of an embodiment of the housing unit.

In various embodiments, one end of the housing unit 14 tapers to a point to form a shallow cone at one of the cylindrical body of the housing unit 14, as seen in FIGS. 2-4. The conical shape helps to facilitate coupling with the tampon member 12 during assembly and also provides support for the tampon member 12 as the tampon member 12 and housing unit 14 are inserted into the vaginal canal during usage.

In various embodiments, the other end of the housing unit 14 is coupled to one end of the cable 16. The cable 16 includes an electric cable 24 coupled with a mechanical cable 26, as shown in FIG. 5. The electric cable 24 occupies the two outer strands of the cable 16, while the mechanical cable 26 is the center strand of the cable 16. The electric cable 24 includes conductive leads 28, 30 in the central core of each of the cable strands to provide an electrical connection. The mechanical cable 26 may be fabricated from a strengthening material or may include internal strengthening components in order to provide mechanical pull strength for removal of the tampon member 12 and housing unit 14 from the vaginal canal after usage.

Inside the housing unit are two cable connectors 32, 34 that connect to the electric cable 24, as seen in FIG. 4. One connector 32 connects to one lead 28 of the electric cable 24 and the other connector 34 connects to the other lead 30 of the electric cable 24. Each connector 32, 34 may be an insulation displacement type of connector. The connection is made during assembly by pushing the one of the leads 28 into the opening of the connector 32 such that the connector 32 pierces the insulation of the lead 28 and makes physical contact with the conductor of the lead without any stripping or removal of the insulation. This procedure is repeated for the other connector 34 and the other lead 30 of the electric cable 24. Other types of connectors are possible that establish a physical connection with the conductors of the electric cable that may involve techniques such as soldering to help establish the connection. However, the insulation displacement connector described above has the advantage that the electrical connection can be established with a sufficient downward force of the cable 16 onto the connectors 32, 34, which can be performed simply during manufacturing without prior stripping of the insulation.

As shown in FIG. 4, in various embodiments, the housing unit also houses the vibration element 20. The vibration element 20 is located on the interior of the housing unit 14 and is coupled to the cable connectors 32, 34. The vibration element 20 includes a motor 36 coupled to a counterweight 38. The motor 36 is a direct current (DC) motor as is known in the art, cylindrical in shape, and includes terminals and a drive shaft 40. A positive voltage terminal 42 is at one end of the motor 36 and is connected to one of the cable connectors 32. A negative voltage terminal 44 is along the curved outer portion of body of the motor 36 and the other cable connector 34 makes contact in this area.

The drive shaft 40 is directly connected to the counterweight 38 such that rotation of the drive shaft 40 results in synchronous rotation of the counterweight 38. The counterweight 38 is generally semi-cylindrical in shape and located offset from the axis of the drive shaft 40 such that angular rotation of the counterweight 38 about the drive shaft 40 axis causes a radial acceleration of the mass of the counterweight 38. The radial acceleration of the counterweight 38 creates a pull on the motor 36 away from its central axis. Thus, continuous rotation of the counterweight 38 generates a continuous pull on the motor 36 and in turn the housing unit 14 and the tampon member 12 which is felt as a vibration.

In various embodiments, the motor 36 and the counterweight 38 are an integrated unit. One example of the integrated unit is the model number Z6CL2A0540721 micro vibration motor, manufactured by JinLong Machinery. It operates on a nominal voltage of 1.3 Volts (V) DC and draws a nominal current of 70 milliAmps (mA). The micro vibration motor provides a vibrational frequency of between 108 Hertz (Hz) and 175 Hz However, vibrational frequencies between 20 Hz and 400 Hz have been found to provide relief for the pain from menstrual cramps.

In other embodiments, the vibration element 20 may be any type of transducing apparatus or mechanism that converts a DC electric voltage to a vibrational motion, such as, but not limited to, a crystal oscillator that supplies an oscillating electric signal to a piezoelectric material or a voice coil to produce vibrations. Transducing mechanisms that utilize a DC voltage as an input are preferable because a limited period of operation of the vibration element is required and a limited lifetime source of DC voltage may be conveniently and reliably supplied by a standard, non-rechargeable electric battery. However, the scope of the invention is not limited to an electrically powered vibration element. Any vibrating mechanism may be used as the vibration element that possesses a limited lifetime of vibration, either naturally or by design, and can be controlled to operate both in a temporary and continuous fashion.

Figures 6, 7, 8:
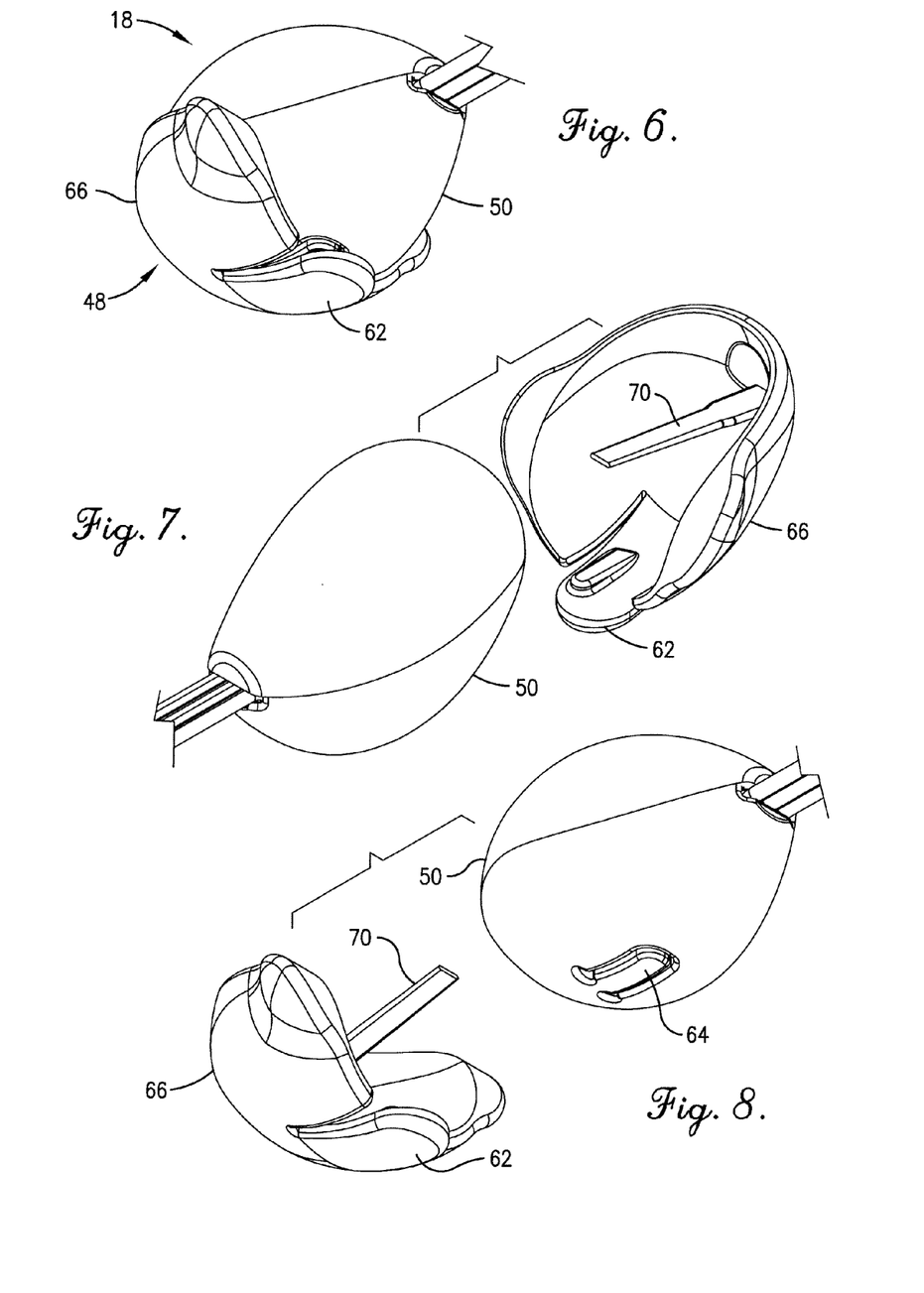
FIG. 6 is a perspective view of a first embodiment of the control unit.
FIG. 7 is an exploded perspective view of a first embodiment of the control unit.
FIG. 8 is an exploded perspective view of a first embodiment of the control unit.
Figures 14, 15, 16:
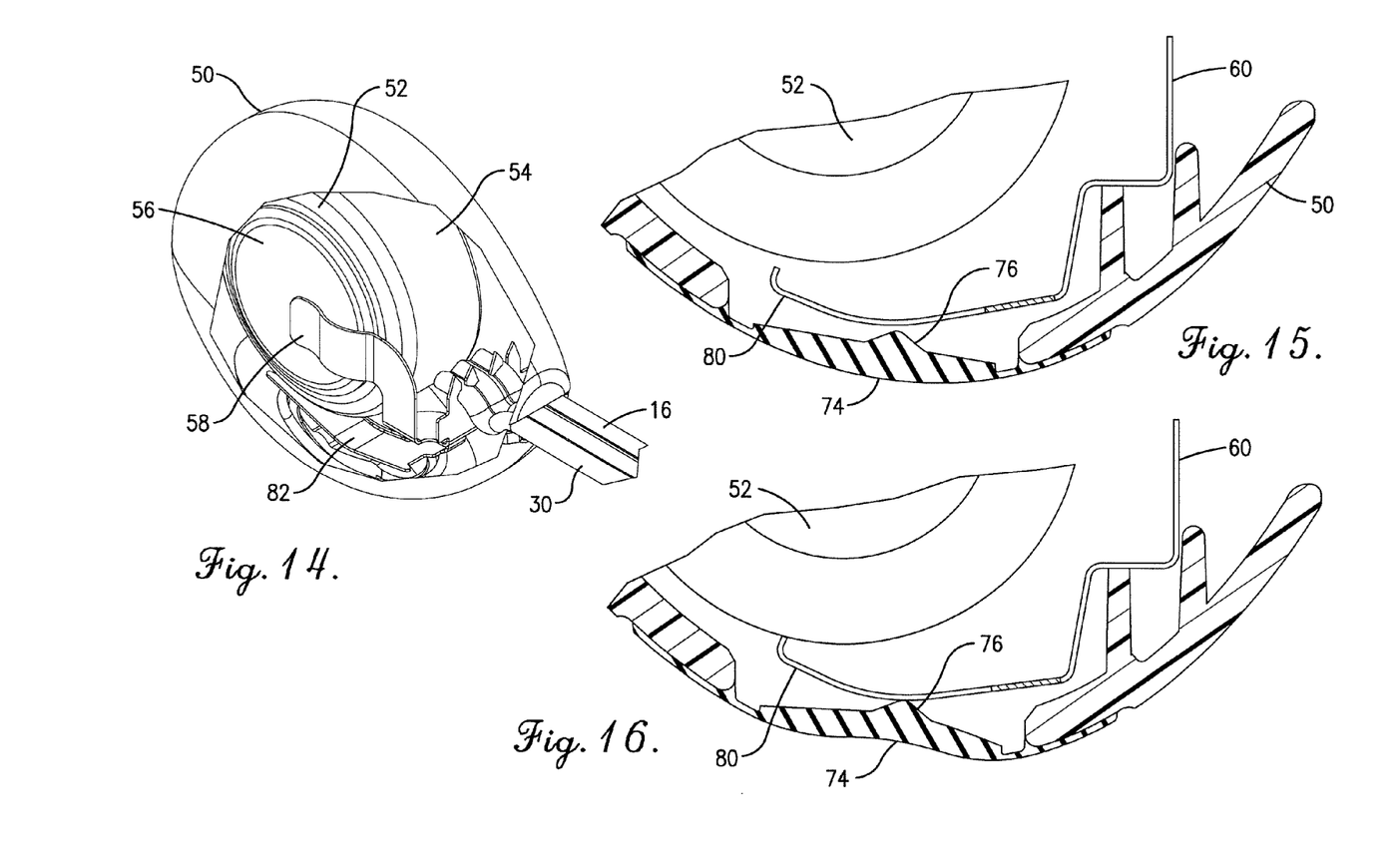
FIG. 14 is a partial sectional view of a second embodiment of the control unit.
FIG. 15 is a sectional view of a second embodiment of the control unit.
FIG. 16 is a sectional view of a second embodiment of the control unit.

The control unit 18 generally provides control of the electrical connection between the vibration element 20 and an electric power source 46, and includes a switch apparatus 48, as seen in FIG. 2. As seen in FIGS. 6-8, the control unit 18 is roughly oval-shaped and includes a shell 50. In various embodiments, the electric power source 46 is housed within the control unit 18, as seen in FIGS. 2 and 14. Typically, the electric power source 46 is a standard, non-rechargeable DC electric battery 52 that supplies 1.5V and fits within the space of the control unit 18, such as the type LR44 battery. A standard, non-rechargeable DC electric battery is most advantageous for use with the apparatus 10 because a non-rechargeable battery naturally has a limited lifetime. Other sources of DC electric voltage are possible for use with the apparatus 10 as long as the source possesses a limited lifetime, either naturally or by design, and can provide an electric power source to connect to a circuit both in a temporary and continuous fashion.

The battery 52 has a positive voltage terminal 54 and a negative voltage terminal 56 and typically the negative voltage terminal 56 is permanently connected through a cable connector 58 within the control unit 18 to one of the electric cable leads 30, as best seen in FIG. 14. The cable connector 58 and its coupling to the electric cable lead 30 are generally the same as the cable connector in the housing unit and the other end of the electric cable. Likewise, other types of connectors are possible. The negative voltage terminal 56 and the electric cable lead 30 to which it is connected are generally considered to be electric ground.

In the control unit, the other cable lead 28 is generally connected to another cable connector 60 in the same manner as the cable connector 58 for the negative voltage terminal 56. However, the electrical connection from the cable lead 28 to the positive voltage terminal 54 of the battery 52 is controlled through the switch apparatus 48.

Figure 9:
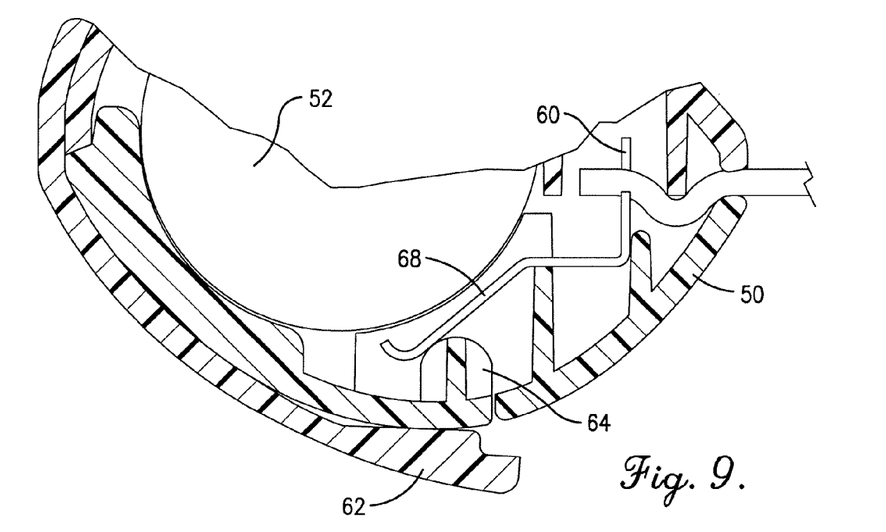
FIG. 9 is a partial sectional view of a first embodiment of the control unit.
Figure 10:
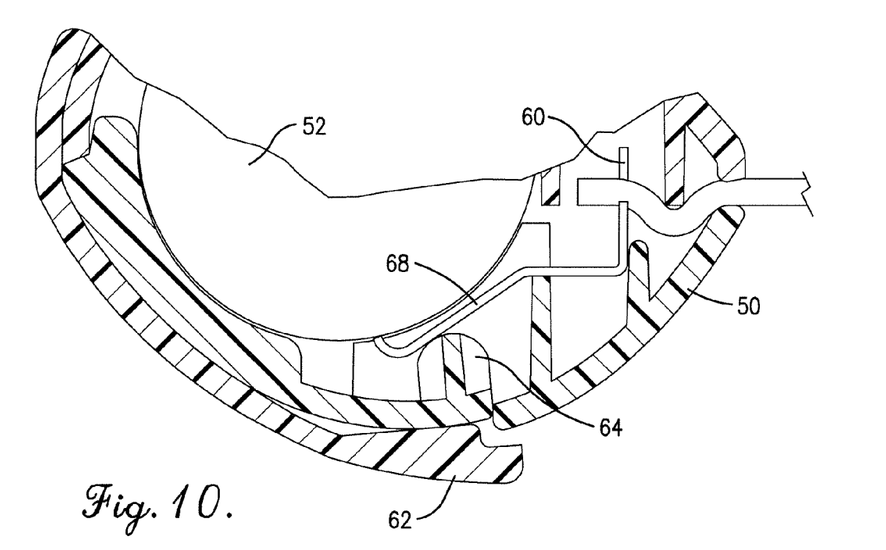
FIG. 10 is a partial sectional view of a first embodiment of the control unit.
Figure 11:
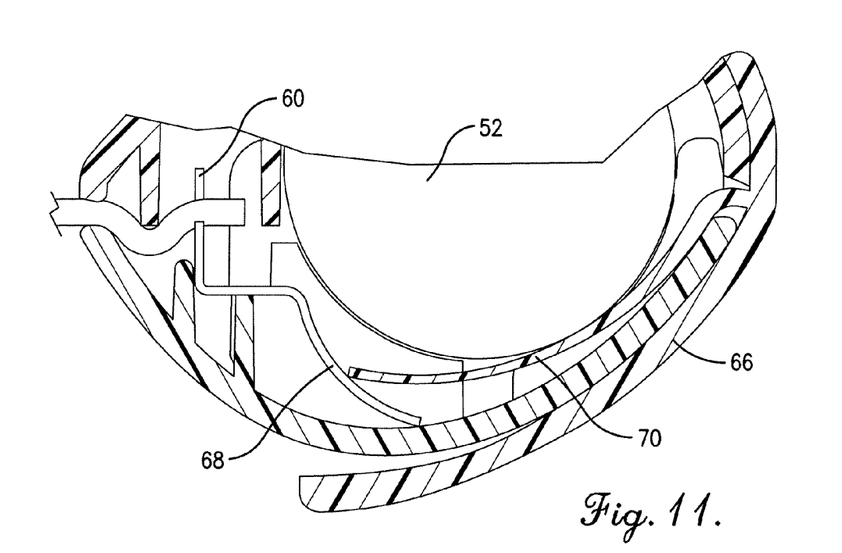
FIG. 11 is a partial sectional view of a first embodiment of the control unit.
Figure 12:
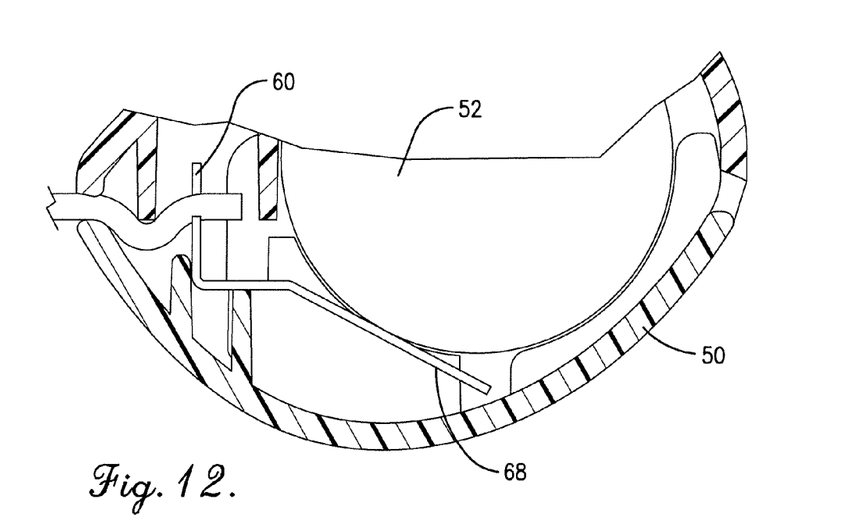
FIG. 12 is a partial sectional view of a first embodiment of the control unit.
Figure 13:
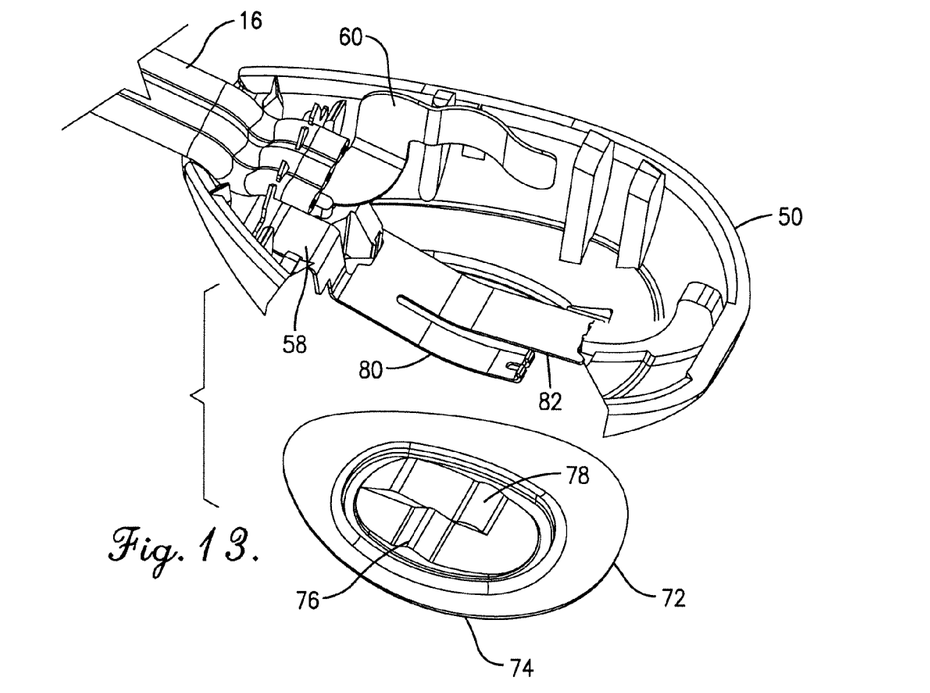
FIG. 13 is a partial exploded view of the interior of a second embodiment of the control unit.

In various embodiments, the switch apparatus 48 includes a momentary button 62, a momentary actuator 64, and a removable cap 66, as shown in FIGS. 6-12. The other cable connector 60 connects the other electric cable lead 28 to a conductive momentary contact arm 68, as shown in FIGS. 9 and 10. Pressure on the momentary button 62 pushes the momentary actuator 64, which in turn pushes the momentary contact arm 68 to make contact with the positive voltage terminal 54 of the battery 52 and initiates temporary operation of the apparatus 10. Removal of the pressure on the momentary button 62 breaks contact between the momentary contact arm 68 and the battery 52 and terminates temporary operation of the apparatus 10. The removable cap 66 includes an insulating tab 70 that extends outward from the inner surface of the removable cap 66 to prevent contact between the positive voltage terminal 56 of the battery 52 and the other cable connector 60, as seen in FIGS. 11 and 12. Removal of the cap 66 from the shell 50 of the control unit 18 also removes the tab 70, thereby allowing contact between the battery 52 and the other cable connector 60, and thus initiating continuous operation of the apparatus 10, which cannot be terminated by replacement of the cap 66 onto the shell 50 as the tab 70 may not be reinserted into the shell 50 to break contact between the battery 52 and the other cable connector 60.

In other embodiments, the switch apparatus 48 includes a two-stage pushbutton 72 that is coupled to the shell 50 of the control unit 18, as seen in FIGS. 13-18. The pushbutton 72 includes a push surface 74, a momentary actuator 76, a continuous actuator 78, a conductive momentary contact arm 80, and a conductive continuous contact arm 82. The momentary actuator 76 and the continuous actuator 78 are coupled to the push surface 74. The momentary contact arm 80 and the continuous contact arm 82 are connected to one another and both are connected to the cable connector 60. The momentary contact arm 80 is bent at a near-right angle close to the free end of the contact arm 80. The continuous contact arm 82 is slightly longer than the space within the shell 50 that it occupies. During assembly, the continuous contact arm 82 is inserted between posts in the shell 50, and due to its oversized length, the continuous contact arm 82 is in compression and thus bends toward the exterior of the shell 50 in order to fit in the space. After the contact arms 80, 82 are properly placed in the shell 50, the momentary actuator 76 is aligned above the momentary contact arm 80 and the continuous actuator 78 is aligned above the continuous contact arm 82.

Figures 17, 18:
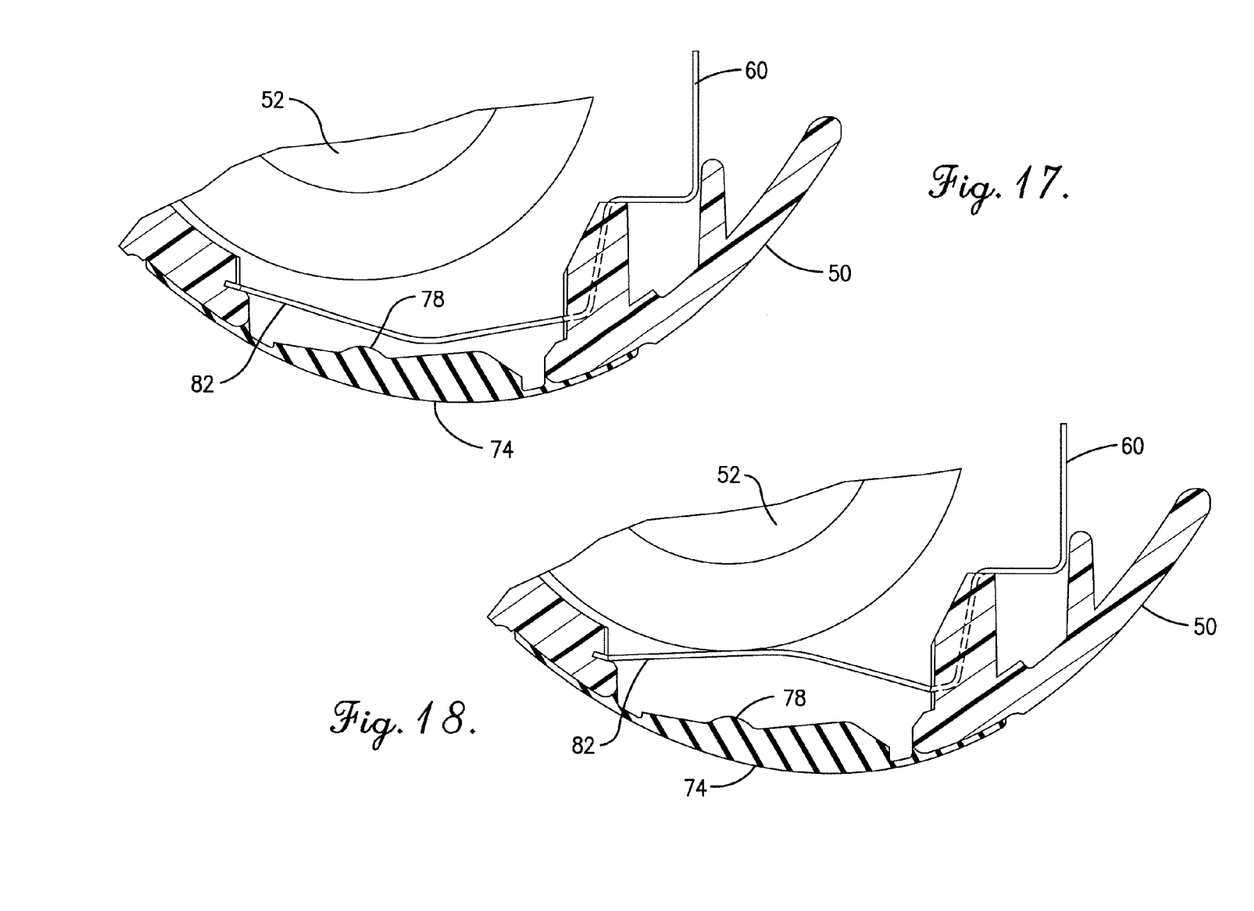
FIG. 17 is a sectional view of a second embodiment of the control unit.
FIG. 18 is a sectional view of a second embodiment of the control unit.

During usage, when a downward force is applied to the push surface 74, both actuators 76, 78 move toward both contact arms 80, 82. The momentary actuator 76 engages the momentary contact arm 80 and pushes it to make contact with the positive voltage terminal 54 of the battery 52, as shown in FIGS. 15 and 16. At this point, temporary operation of the apparatus 10 occurs until the force on the push surface 74 is removed. When a force is applied to the push surface 74, the continuous actuator 78 also engages the continuous contact arm 82 while the momentary actuator 76 causes the momentary contact arm 80 to contact the battery 52 and initiate temporary operation of the apparatus 10. Temporary operation is terminated with removal of the force. During this time, the continuous contact arm 82 is bending only slightly from the pressure of the continuous actuator 78 and will return to its normal position when the pressure is removed as shown in FIG. 17. However, if the force on the push surface 74 increases, the continuous actuator 78 will push the continuous contact arm 82 towards the center of the shell 50 to a point where the continuous contact arm 82 will no longer be able to return to its normal position. Due to the compression exerted on the continuous contact arm 82 by the shell, the continuous contact arm 82 will invert and pull the momentary contact arm 80 into continuous contact with the battery 52 as shown in FIG. 18. The continuous contact arm 82 and the momentary contact arm 80 will remain in these positions even when the force on the push surface 74 is removed, thereby providing a continuous electrical connection between the battery 52 and the electric cable 24, and thus initiating continuous operation of the apparatus 10 that may not be terminated under normal circumstances.

Figure 19:
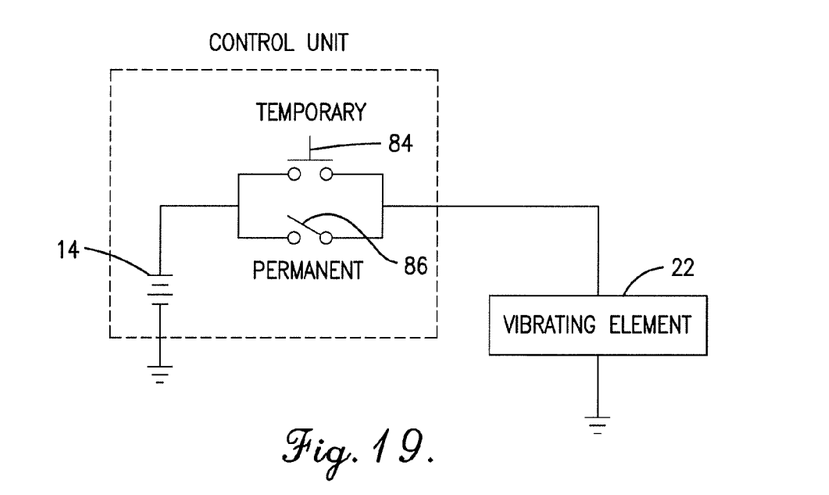
FIG. 19 is a schematic of the electric circuit of the apparatus.

The electrical operation of various embodiments of the apparatus 10 can also be illustrated in the schematic of FIG. 19. The electric power source 46 is shown as a DC voltage source. The switch apparatus of both embodiments discussed above is shown as a normally-open pushbutton switch 84 in parallel with a single-pole single-throw switch 86. One side of the two parallel switches 84, 86 is in series with the positive voltage terminal of the electric power source 46. The other side of the two parallel switches 84, 86 is connected to the vibration element 20. And the negative voltage terminal of the electric power source 46 is connected through ground to the vibration element 20.

The normally-open pushbutton switch 84 represents the momentary button switch 62 and the momentary contact arm 80. The single-pole single-throw switch represents the removable cap 66 and the continuous contact arm 82, wherein once the single-pole single-throw switch 86 is closed, it cannot be reopened under normal circumstances. As seen in FIG. 19, the current path from the electric power source 46 to the vibration element 20 is complete whenever either the normally-open pushbutton switch 84 is pressed or the single-pole single-throw switch 86 is closed. As noted on the schematic, pressing the normally-open pushbutton switch 84 creates a temporary circuit, while closing the single-pole single-throw switch 86 creates a continuous circuit, thereby creating two modes of operation for the apparatus 10—temporary and continuous. The temporary mode may be utilized during the manufacturing process to test and momentarily verify the operation of the apparatus 10 as a quality control step before shipping of the product. The continuous mode is utilized during normal usage.

The apparatus may be used in the following manner. The user may wish to verify the operation of the apparatus 10 or perhaps to verify the body's reaction to the sensation of the vibration. This can be accomplished by activating the switch apparatus 48 in the temporary operation mode as described for various embodiments above. If the user is satisfied with the performance of the apparatus 10, the user may insert the tampon member 12 coupled with the housing unit 14 only into the vaginal canal. Thus, the control unit 18 and a portion of the cable 16 remain outside the body. The user may once more activate the temporary operation mode. Again, if the user is satisfied with the performance of the apparatus 10, the continuous operation mode may be activated. The apparatus 10 operates continuously until the electric power source 46 drains and vibration ceases. At this time, the user may remove the tampon member 12 and housing unit 14 by pulling on the cable 16. Once the tampon member 12 and housing unit 14 are extracted, the user may dispose of the entire apparatus 10.

Generally, it is desirable for a limited lifetime of the electric power source 46 and thereby, the vibration of the apparatus 10, to encourage single usage of the tampon apparatus 10. Reuse of the housing unit 14 with a different tampon member 12 may be possible but is strongly not recommended in order to avoid bacterial-related infections that may cause Toxic Shock Syndrome.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A vibrating tampon apparatus, the apparatus comprising:
a vibration element operable to provide vibratory motion;
a housing unit for housing the vibration element, the surface of the housing unit including at least three spaced apart external retaining elements protruding from and distributed over a surface of the housing unit; and
a tampon member operable to cover at least a portion of the housing unit, the tampon member being formed of an absorbent material, and securely fastened to the housing unit such that the barbs and stubs oppose removal of the tampon member, the tampon member and the housing unit being appropriately dimensioned so as to be received in a female's vaginal canal.

2. The apparatus of claim 1, further comprising an electric power source, located externally from the housing unit and operable to supply electric power to the vibration element.

3. The apparatus of claim 2, further comprising a control unit, collocated with the electric power source, operable to control an electrical connection from the electric power source to the vibration element.

4. The apparatus of claim 3, wherein the control unit includes a removable cap, that when removed provides continuous operation of the apparatus for the lifetime of the electric power source.

5. The apparatus of claim 3, wherein the control unit further includes a momentary button, that when activated provides temporary operation of the apparatus.

6. The apparatus of claim 3, wherein the control unit further includes a pushbutton, that when pushed with a lesser force provides temporary operation of the apparatus and when pushed with a greater force provides operation of the apparatus for the lifetime of the electric power source.

7. The apparatus of claim 3, further comprising an electric cable providing an electrical connection between the control unit and the vibration element.

8. The apparatus of claim 7, further comprising a mechanical cable coupled to the electric cable, providing mechanical pull strength for a connection between the control unit and the housing unit.

9. The apparatus of claim 1, wherein at least a portion of the exterior of the housing unit is coated with an adhesive.

10. The apparatus of claim 1, wherein the tampon member includes an analgesic and other medicaments to provide pain relief upon contact with the walls of the vaginal canal.

11. The apparatus of claim 1, wherein the vibration element is an electric motor that rotates a counterweight.

12. The apparatus of claim 1, wherein the vibration element includes a piezoelectric transducer.

13. The apparatus of claim 1, wherein the frequency of the vibratory motion is from 20 Hertz to 400 Hertz.

14. The apparatus of claim 1, wherein the retaining elements include a plurality of elongated protruding barbs and a plurality of shortened protruding stubs, wherein the elongated barbs are longer than the shortened stubs.

15. A vibrating tampon apparatus, the apparatus comprising:
a vibration element operable to provide vibratory motion;
a water resistant housing unit for housing the vibration element, the surface of the housing unit including a plurality of elongated protruding barbs and a plurality of shortened protruding stubs;
a tampon member operable to cover at least a portion of the housing unit, the tampon member being formed of an absorbent material, and securely fastened to the housing unit such that the barbs and stubs oppose removal of the tampon member, the tampon member and the housing unit being appropriately dimensioned so as to be received in a female's vaginal canal;
an electric power source operable to supply electric power to the vibration element, the electric power source being located externally from the housing unit;
a control unit operable to control an electrical connection from the electric power source to the vibration element, the control unit being collocated with the electric power source, and including:
   a removable cap, that when removed provides continuous operation of the apparatus for the lifetime of the electric power source, and
   a momentary button, that when activated temporary operation of the apparatus;
an electric cable providing an electrical connection between the control unit and the vibration element; and
a mechanical cable providing mechanical pull strength for a connection between the control unit and the housing unit, the mechanical cable being coupled to the electric cable.

16. The apparatus of claim 15, wherein the tampon member includes an analgesic and other medicaments to provide pain relief upon contact with the walls of the vaginal canal.

17. A vibrating tampon apparatus, the apparatus comprising:
   a vibration element operable to provide vibratory motion;
   a housing unit for housing the vibration element, the housing unit including a plurality of external retaining elements extending outward from a surface of the housing unit, wherein the retaining elements are spaced apart along both a longitudinal axis and a transverse axis perpendicular to the longitudinal axis; and
   a tampon member operable to cover at least a portion of the housing unit, the tampon member having an elongated hollow cylindrical shape with a hemispherical dome at one end and forming an opening at an opposing end, the tampon being formed of an absorbent material, and securely fastened to the housing unit by the plurality of external retaining elements, the tampon member and the housing unit being appropriately dimensioned so as to be received in a female's vaginal canal.

18. The vibration tampon apparatus of claim 17, wherein the plurality of external retaining elements includes a plurality of elongated protruding barbs and a plurality of shortened protruding stubs, such that the barbs and stubs oppose removal of the tampon member, wherein the elongated barbs are longer than the shortened stubs.

19. A vibrating tampon apparatus, the apparatus comprising:
   a vibration element operable to provide vibratory motion;
   a housing unit for housing the vibration element, the housing unit including a plurality of external retaining elements protruding from and distributed over a surface of the housing unit, wherein the retaining elements are spaced apart from each other and extend less than 50% around a circumference of the housing unit; and
   a tampon member operable to cover at least a portion of the housing unit, the tampon member being formed of an absorbent material, and securely fastened to the housing unit by the plurality of external retaining elements, the tampon member and the housing unit being appropriately dimensioned so as to be received in a female's vaginal canal.

20. The vibrating tampon apparatus of claim 19, wherein the plurality of external retaining elements comprises at least three spaced apart, discrete external retaining elements.

21. The vibrating tampon apparatus of claim 19, wherein the external retaining elements are distributed over at least 40% of the surface of the housing unit.

22. The vibrating tampon apparatus of claim 19, wherein the housing unit has a length and a circumference, the external retaining elements each have a length and a width, and the length and the width of the retaining elements are each less than the circumference of the housing unit.

23. The vibrating tampon apparatus of claim 19, wherein the housing unit has a length and a circumference, and a lateral distance between at least two of the retaining elements is equal to at least 30% of the length of the housing unit.

24. The vibrating tampon apparatus of claim 19, wherein none of the retaining elements circumscribe the housing unit.

* * * * *